United States Patent [19]

Bloom et al.

[11] 4,006,151
[45] Feb. 1, 1977

[54] PRECURSORS OF β-AZA-DISUBSTITUTED AMINO STYRYL DYES

[75] Inventors: Stanley M. Bloom, Waban; Alan L. Borror; Richard B. Greenwald, both of Lexington, all of Mass.

[73] Assignee: Polaroid Corporation, Cambridge, Mass.

[22] Filed: June 25, 1975

[21] Appl. No.: 590,144

Related U.S. Application Data

[60] Continuation-in-part of Ser. No. 399,456, Sept. 21, 1973, abandoned, Division of Ser. No. 261,270, June 9, 1972, Pat. No. 3,794,465.

[52] U.S. Cl. .................. 260/294.8 F; 260/283 S; 260/286 Q; 260/298; 260/304 R; 260/307 D; 260/240.8
[51] Int. Cl.² ................................. C07D 213/34
[58] Field of Search .................... 260/294.8 F

[56] References Cited
OTHER PUBLICATIONS

Bloom et al., Chem. Abstracts, vol. 81, (4), Item no. 19,248f, July 29, 1974.

*Primary Examiner*—Alan L. Rotman
*Attorney, Agent, or Firm*—Philip G. Kiely

[57] ABSTRACT

Novel substantially colorless dye precursors represented by the formula

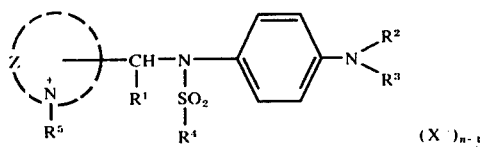

wherein $R^1$ is hydrogen or alkyl; $R^2$, $R^3$ and $R^5$ is alkyl; $R^4$ is alkyl or phenyl; Z, taken with N, represents the atoms necessary to make up a pyridine, quinoline, benzoxazole, benzthiazole or benzselenazole radical; X is an acid anion; and $n$ is 1 when $R^5$ carries a negative charge and 2 when $R^5$ is electrically neutral.

9 Claims, No Drawings

PRECURSORS OF β-AZA-DISUBSTITUTED AMINO STYRYL DYES

CROSS-REFERENCE TO OTHER APPLICATIONS

This application is a continuation-in-part of U.S. Pat. Application Ser. No. 399,456 filed Sept. 21, 1973, now abandoned which is a division of U.S. Pat. Application Ser. No. 261,270 filed Jun. 9, 1972; now U.S. Pat. No. 3,794,465, issued Feb. 26, 1974.

BACKGROUND OF THE INVENTION

U.S. Pat. No. 3,794,465 discloses photographic film units which incorporate intermediate the photosensitive silver halide emulsion layer and a transparent support, a substantially colorless precursor of a dye. This precursor is converted into a dye, a colored species which will absorb light which otherwise might fog the photoexposed silver halide emulsion. Since the precursor is initially colorless, the location of the precursor in the film unit does not interfere with the exposure of the silver halide emulsion. The precursor is converted to its colored form by contact with alkali.

In a preferred embodiment, the dye produced from the above-described precursor is a silver halide desensitizing agent. Thus, instead of a light filtering mechanism, a silver halide desensitizing mechanism may be employed to protect the silver halide emulsion layer from post-exposure fogging. While the same materials can be employed to perform the two described functions, it should be understood that the quantity employed is generally much less for the silver halide desensitizing agent than for the filter dye.

The present invention is directed to novel compositions for use as the above-described dye precursors.

Summary

The novel compounds of the present invention comprise a substantially colorless precursor of a β-azadisubstituted amino styryl dye represented by the formula:

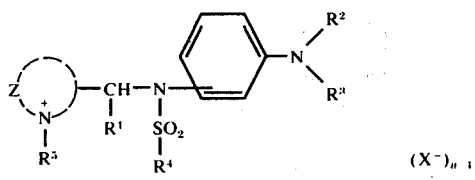

wherein $R^1$ is hydrogen or alkyl; preferably 1 to 4 carbon alkyl; $R^2$ $R^3$ and $R^5$ are alkyl, preferably 1 to 4 carbon alkyl, more preferably, methyl or ethyl; $R^4$ is alkyl or phenyl, preferably 1 to 4 carbon alkyl or phenalkyl; Z, taken with N, represents the carbon atoms necessary to make up a pyridine, quinoline, benzoxazole, benzthiazole or benzselenazole radical; X is an acid anion; and n is 1 when $R^5$ carries a negative charge and 2 when $R^5$ is electrically neutral.

The anion designated X represents those anionic radicals customary in the art, for example, chloride, bromide, iodide, p-toluene sulfonate, acetate, propionate, nitrate, sulfate, etc. Preferably, the anion is the fluorosulfonate radical $.FSO_3^-$.

As stated above, the compounds of the present invention are normally inert with respect to silver halide and substantially colorless. Upon contact with an alkaline processing composition the chromophoric group is generated. The following equation illustrates the reaction which the compounds of the present invention undergo.

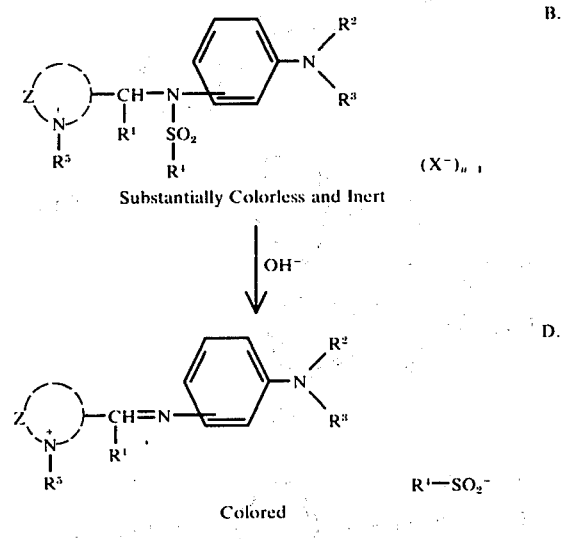

From the foregoing equation it will be seen that the base of alkaline processing composition serves to release the alkyl or aryl sulfonic acid to generate the chromophoric group C = N forming a colored compound known to the art to be a strong desensitizer for silver halide.

As examples of specific compounds within the scope of the present invention mention may be made of the following:

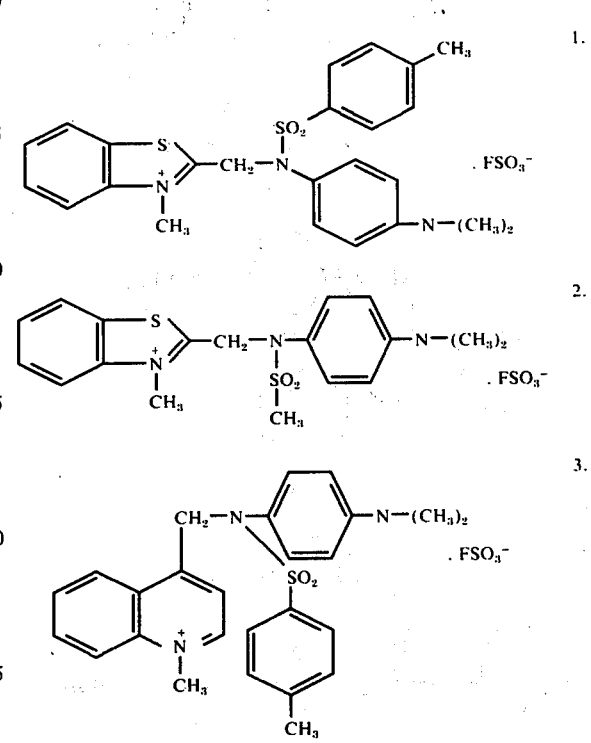

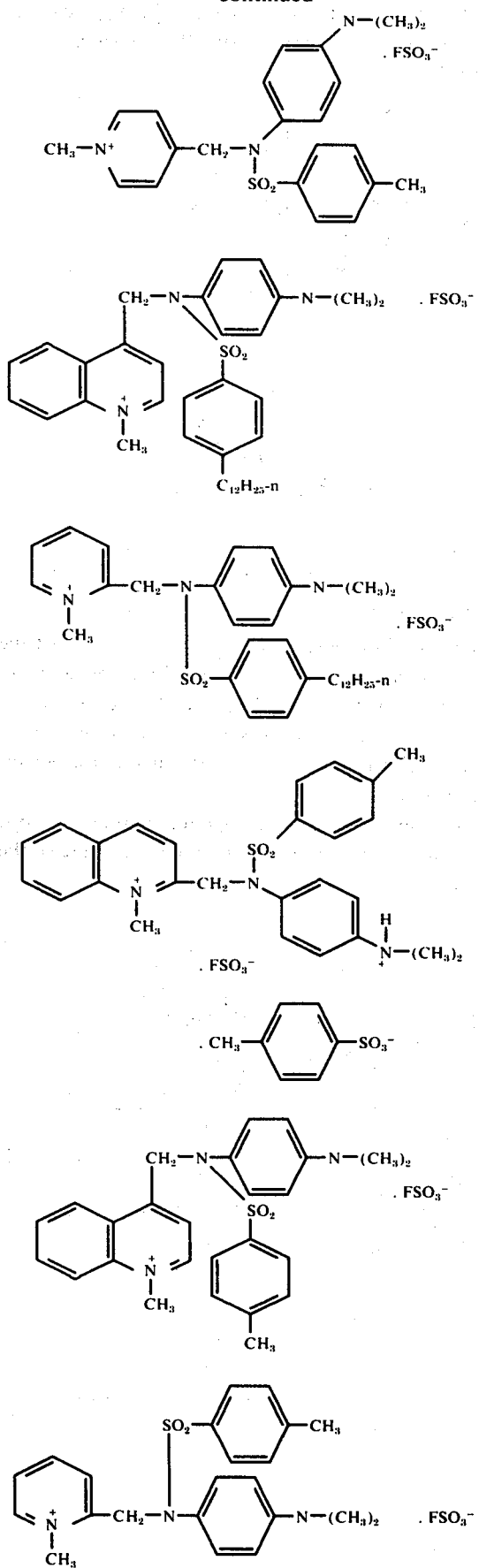
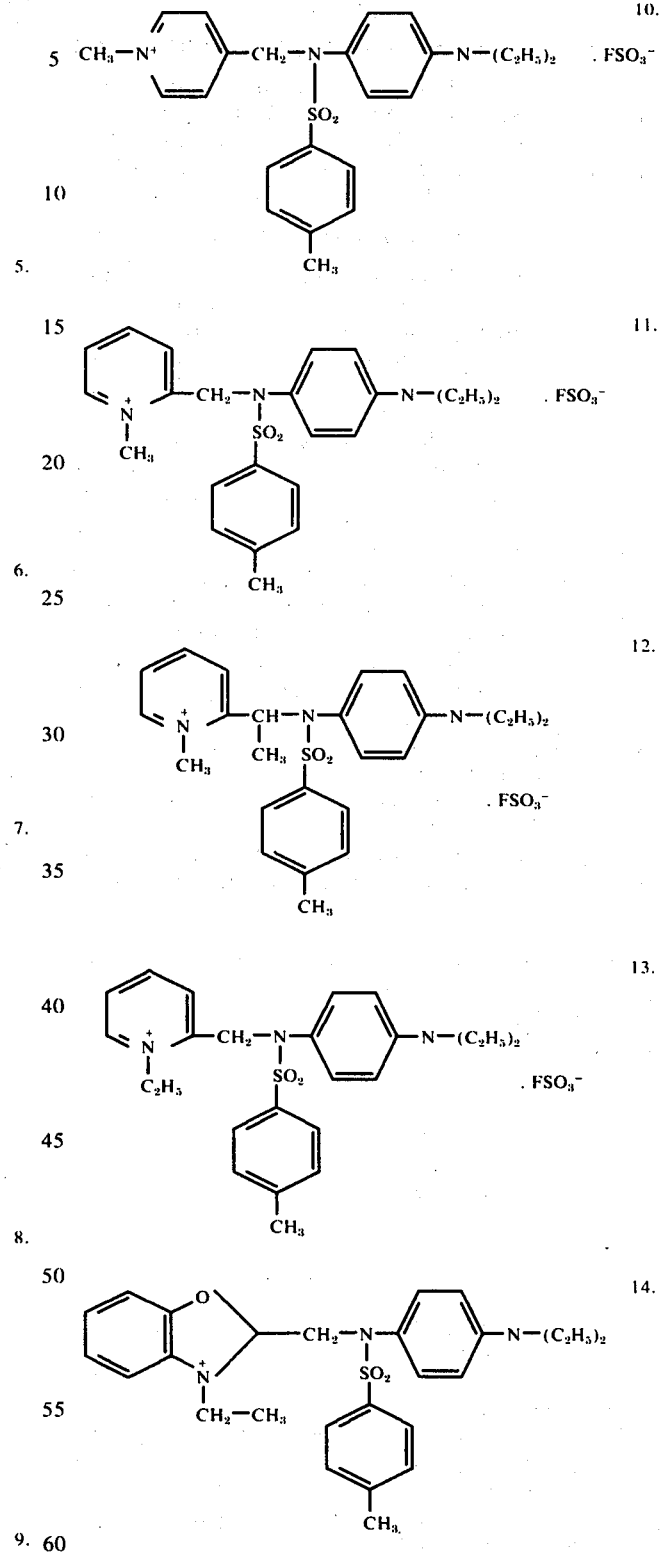
The following non-limiting examples illustrate the preparation of the desensitizing agent precursors of the present invention.

EXAMPLE I

Compound No. 1 was prepared by dissolving

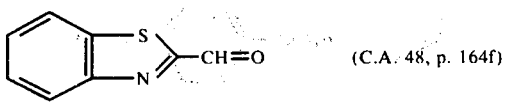  (C.A. 48, p. 164f)

(2.7 g. ) and N,N-dimethyl-p-phenylenediamine (5.0 g.) in 25 ml. of toluene and refluxing the mixture for 2 hours. The mixture was filtered and cooled and the solid was washed with cold water giving 2.6 g. of

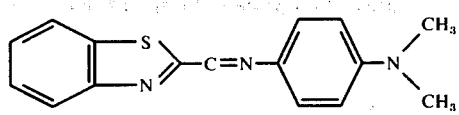

m.p. 173-175° C. Analysis: Calculated C, 68.38 H, 5.38 N, 4.96 S, 11.41 Found C, 68.06 H, 5.30 N, 4.79 S, 11.36, which was reduced using Raney nickel in ethyl acetate to provide

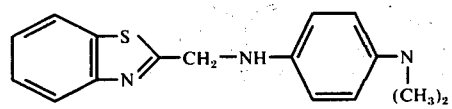

m.p. 93.5°–95° C. Analysis: Calculated C, 67.90; H, 6.06; N, 14.85; S, 11.33; Found C, 67.91; H, 5.95; N, 14.78; S, 11.07. The last-mentioned compound (1.0 g.) was dissolved in 10 ml. of pyridine and 1.5 g. p-toluene sulfonyl chloride was added. The mixture was stirred for 15 minutes. Water was added to precipitate

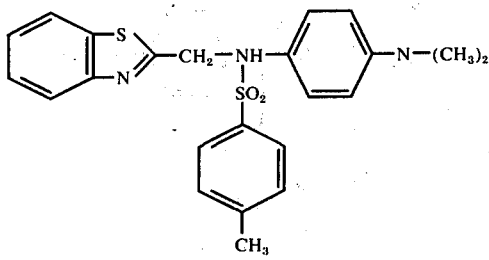

The last-named compound was quaternized in ethyl acetate using 2.36 g. of the compound in 100 ml. of ethyl acetate and 500 mg. of methylfluorosulfonate. The mixture was allowed to stand for 15 minutes. The supernatant liquid was decanted, an equal volume of ether added and the mixture allowed to stand overnight. Compound No. 1 was filtered off and found to melt at 104°–107° C.

EXAMPLE II

The procedure and materials of Example I were repeated except that methane sulfonyl chloride was employed instead of p-toluenesulfonyl chloride to produce a microcrystalline solid, Compound No. 2.

EXAMPLE III

Compound No. 3 was prepared by mixing 9.8 g. of

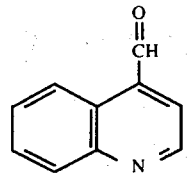

(J.A.C.S. 69, 1219 (1947) m.p. about 150° C., and 8 g. of

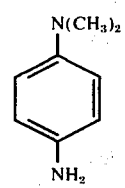

in 100 ml. of benzene. 100 mg. of p-toluene sulfonic acid was added and the mixture refluxed for 1 hour, using a Dean-Stark trap, cooled, evaporated to ⅓ the volume and filtered to provide a red solid

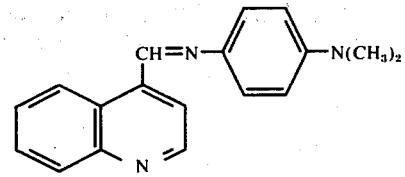

m.p. 151°–154° C. Analysis: Calculated C, 78.61; H, 6.23; N, 15.28; Found C, 78.62; H, 6.11; N, 15.25, 8 g. of the last shown compound was triturated with 50 ml. of methanol, and 8 g. of sodium borohydride was added in small increments. After stirring for 15 minutes, the solution was diluted with 250 ml. water and the precipitate filtered and washed with carbon tetrachloride. Hexane is then added and the precipitate filtered to provide

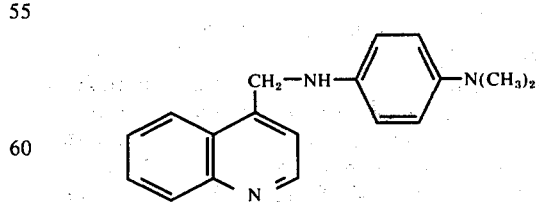

m.p. 105°–107° C. 4 g. of the last shown compound were reacted with 4 g. of p-toluene sulfonyl chloride to provide

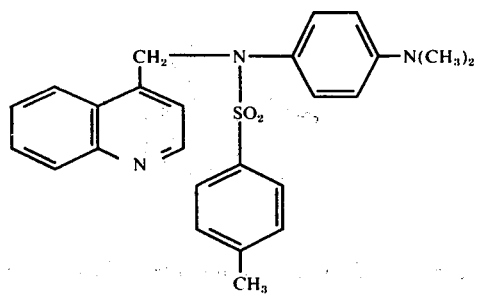

m.p. 157°–159° C. The compound was quaternized with methylfluorosulfonate in substantially the same manner as Example I to provide Compound No. 3.

27.2 g. of

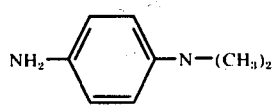

and 24 g. of

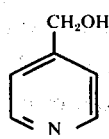

were reacted according to the procedure of Proc. of Chem. Pharm. Bull., Japan 13, 1135, to provide

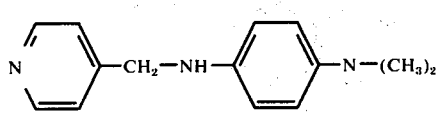

5.0 g. of which was reacted in 50 ml. of pyridine and 3.8 g. p-toluenesulfonyl chloride to provide

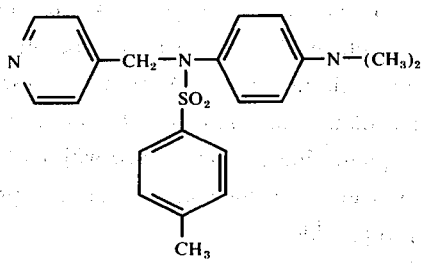

m.p 179°–180° C. Analysis: Calculated; C, 66.20; H, 6.09; N, 11.03; Found C, 65.96; H, 5.83; N, 10.48.

Quaternization was accomplished substantially according to the procedure of Example II to provide Compound No. 4 melting at 145°–148° C. (Recrystallization from iso-propanol.) Analysis: Calculated C, 53.27; H, 5.28; N, 8.47; S, 12.93; F, 3.83 Found C, 52.31; H, 5.39 N, 8.46 S, 13.07 F, 4.05.

EXAMPLE V

Example IV was repeated except that p-dodecylbenzenesulfonyl chloride was used instead of p-toluene sulfonyl chloride to provide Compound No. 5.

EXAMPLE VI

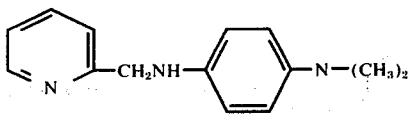

m.p. 70°–72° C. (Recrystallized from ethyl acetate-hexane.) Analysis: Calculated C, 74.07; H, 7.55; N, 18.51; Found; C, 74.57; H, 7.33; N, 18.18.

prepared according to the procedure of Proc. of Chem. Pharm. Bull., Japan 13, 1135, was reacted with 4.0 g. of p-toluenesulfonyl chloride in 50 ml. of pyridine to provide

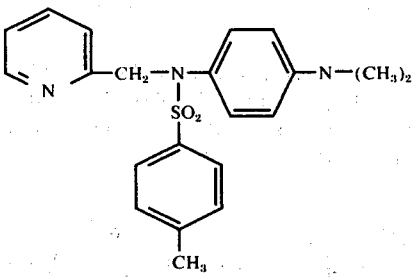

m.p. 145°–147° C. (Recrystallized from ethanol.) Analysis: Calculated C, 66.20 H, 6.09; N, 11.03; Found C, 65.79; H, 6.11; N, 10.85.

4.5 g. of the last-named Compound was dissolved in 40 ml. of pyridine and reacted with 6.9 g. of p-dodecylbenzenesulfonyl chloride to provide

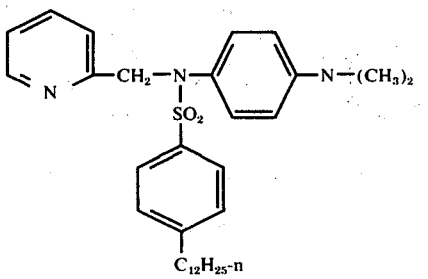

m.p. 95°–97° C. Analysis: Calculated C, 71.70; H, 8.46; N, 7.84 Found C, 71.85; H, 8.47; N, 7.39.

Quaternization was carried out according to the procedure of Example II to provide Compound No. 6 as a microcrystalline solid.

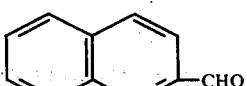

prepared according to the procedure of J.A.C.S. 63, 2654 (1941), 13 g. of

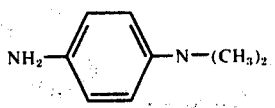

and 10 g. of p-toluenesulfonic acid in 100 ml. benzene was refluxed with a Dean-Stark trap until the mixture ceases to azeotrope. The mixture was concentrated to ½ volume and filtered. The resulting solid

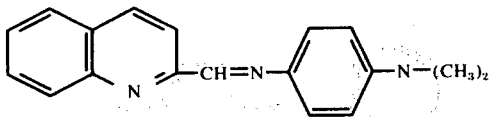

m.p. 143°–145° C. Analysis: Calculated C, 78,61; H, 6.23; N, 15.28; Found C, 78.73; H, 6.54; N, 14.93. was reduced with sodium borohydride according to the procedure set forth in Example III to give

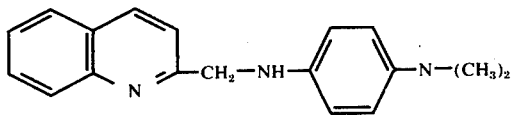

m.p. 116°–118° C. Analysis: calculated C, 78.04; H, 6.55; N, 15.17; Found; C, 78.63; H, 6.78; N, 14.90. and then reacted with p-toluenesulfonyl chloride as described in Example II to provide

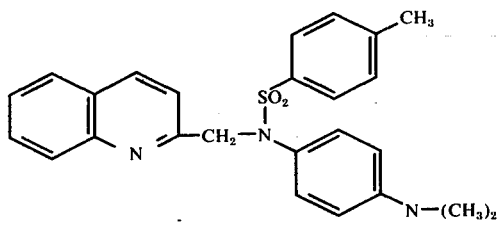

m.p. 132°–134° C.

Quarternization was carried out by dissolving 1.12 g. of the last-named compound in 100 ml. ethyl acetate to which 480 g. toluenesulfonic acid was added. The mixture was evaporated to dryness and the solid azeotroped with benzene. The resulting salt was stirred overnight in 2 l. of ethyl acetate and 300 mg. of methylfluorosulfonate. The mixture was filtered and dryed to provide Compound No. 7 melting at 135°–140° C.

EXAMPLE VIII

Compound No. 12 was prepared employing 2-acetylpyridine (12.1 g. ) N,N-diethyl-p-phenylenediamine (16.4 g.), in 150 ml toluene and 5 mg. of p-toluenesulfonic acid according to the procedure of Example III. The product showed a melting point of 152°–155° C. with decomposition.

EXAMPLE IX

Compound No. 10 was prepared according to the procedure of Example IV except that N,N-diethyl-p-phenylene diamine was used instead of N,N-dimethyl-p-phenylene diamine. The product melted at 121°–123° C. Analysis: Calculated; C, 55.04; H, 5.77; N, 8.03 Found C, 55.22; H. 6.12; N, 8.04.

EXAMPLE X

Compound No. 11 was prepared according to the procedure of Example IX except that 2-pyridylcarbinol was used instead of N-pyridylcarbinol. The product melted at 161°–163° C. Analysis: Calculated C, 55.05; H, 6.65; N, 10.26; Found C, 55.20 H, 6.63; N, 10.21.

EXAMPLE XI

Compound No. 13 was prepared according to the procedure of Example X except that quaternization was carried out using ethylfluorosulfonate. The product melted at 148°–150° C.

EXAMPLE XII

Compound No. 14 was prepared according to the procedure of Example II except that

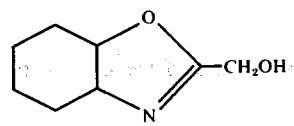

was used instead of 2-pyridylcarbinol. m.p. 162°–165° C.

Since certain changes may be made in the above compositions without departing from the scope of the invention herein involved, it is intended that all matter contained in the above description should be interpreted as illustrative and not in a limiting sense.

I claim:
1. A compound represented by the formula:

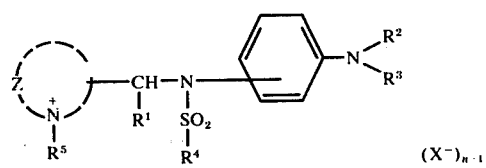

wherein $R^1$ is hydrogen or 1 to 4 carbon alkyl; $R^2$, $R^3$ and $R^5$ is 1 to 4 carbon alkyl; $R^4$ is 1 to 4 carbon alkyl or phenyl; Z, taken with N, represents the atoms necessary to make up pyridine radical; X is an acid anion; and n is 1 when $R^5$ carries a negative charge and 2 when $R^5$ is electrically neutral.

2. The compound as defined in claim 1 wherein $R^2$ and $R^3$ are methyl groups.

3. The compound as defined in claim 1 wherein $R^2$ and $R^3$ are ethyl groups.

4. The compound as defined in claim 1 wherein $R^4$ is

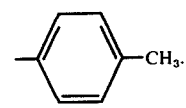

5. The compound as defined in claim 1 wherein $R^4$ is

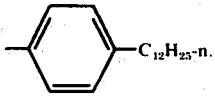
6. The compound as defined in claim 1 wherein $R^5$ is methyl.
7. The compound as defined in claim 1 wherein $R^5$ is ethyl.
8. The compound as defined in claim 1 wherein said compound is:
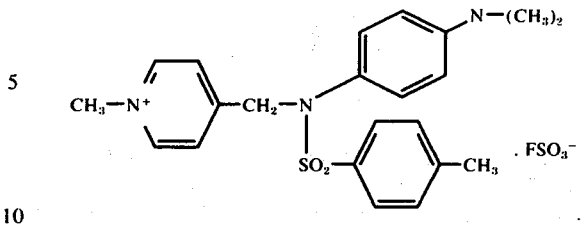
9. The compound as defined in claim 1 wherein said compound is:
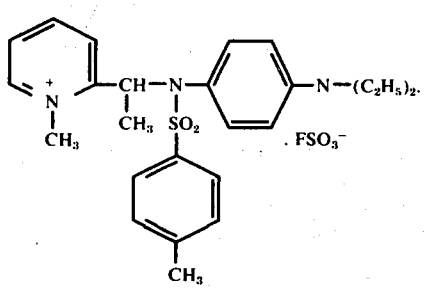
* * * * *